(12) United States Patent
Koop (10) Patent No.: US 8,704,530 B2
(45) Date of Patent: Apr. 22, 2014

(54) LEAD ADAPTER FOR TESTING PACING THRESHOLDS ACROSS MULTIPLE VECTORS AT IMPLANT

(75) Inventor: Brendan E. Koop, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 358 days.

(21) Appl. No.: 13/205,794

(22) Filed: Aug. 9, 2011

(65) Prior Publication Data

US 2012/0153967 A1    Jun. 21, 2012

Related U.S. Application Data

(60) Provisional application No. 61/425,529, filed on Dec. 21, 2010.

(51) Int. Cl.
*G01R 27/28* (2006.01)
(52) U.S. Cl.
USPC .............................. 324/600; 324/612; 324/539
(58) Field of Classification Search
USPC .............. 324/600, 612, 615, 76.11, 71.1, 538
See application file for complete search history.

(56) References Cited

U.S. PATENT DOCUMENTS

| | | | |
|---|---|---|---|
| 7,633,023 B1 * | 12/2009 | Cappa et al. | 200/51.06 |
| 2004/0230268 A1 | 11/2004 | Huff et al. | |
| 2005/0177199 A1 | 8/2005 | Hansen et al. | |
| 2006/0258193 A1 | 11/2006 | Hoecke et al. | |
| 2008/0255630 A1 | 10/2008 | Arisso et al. | |
| 2010/0018062 A1 | 1/2010 | Stravitz | |
| 2011/0160824 A1 | 6/2011 | Ware et al. | |
| 2012/0130397 A1 | 5/2012 | Reddy et al. | |

OTHER PUBLICATIONS

International Search Report and Written Opinion issued in PCT/US2011/047060, mailed Jan. 23, 2012, 14 pages.

* cited by examiner

*Primary Examiner* — Vincent Q Nguyen
(74) *Attorney, Agent, or Firm* — Faegre Baker Daniels LLP (57) ABSTRACT

An adapter is used in conjunction with a testing device to test pacing thresholds of an implanted lead. A main body of the adapter includes a plurality of adapter contacts that are configured to electrically couple to the plurality of connector contacts. A connector module includes a first port configured to couple to a first testing device connector and a second port configured to couple to a second testing device connector. A switch assembly includes a plurality of actuatable elements each associated with one of the adapter contacts. The actuatable elements are each selectably actuatable between a first state that electrically couples the associated adapter contact to the first port, a second state that electrically couples the associated adapter contact to the second port, and a third state that electrically decouples the associated adapter contact from the first and second ports.

20 Claims, 4 Drawing Sheets

LEAD ADAPTER FOR TESTING PACING THRESHOLDS ACROSS MULTIPLE VECTORS AT IMPLANT

CROSS-REFERENCE TO RELATED APPLICATION

This application claims priority to Provisional Application No. 61/425,529, filed Dec. 21, 2010, which is herein incorporated by reference in its entirety.

TECHNICAL FIELD

The present invention relates to implantable medical devices. More particularly, the present invention relates to a lead adapter for testing pacing thresholds across multiple vectors at lead implant.

BACKGROUND

Various types of medical electrical leads for use in cardiac rhythm management (CRM) and neurostimulation applications are known. In CRM applications, for example, such leads are frequently delivered intravascularly to an implantation location on or within a patient's heart, typically under the aid of fluoroscopy. Once implanted, the lead is coupled to a pulse generator or other implantable device for sensing cardiac electrical activity, delivering therapeutic stimuli, and/or for performing some other desired function within the body. Such leads often include a distal, conductor end which contacts the heart tissue, and a proximal, terminal end which is connected to the pulse generator. The conductor end of the lead typically includes one or more features such as an active fixation helix or a number of passive tines to facilitate securing the lead to the heart tissue. The terminal end of the lead, in turn, includes one or more electrical contacts that are electrically connected to the electrodes on the terminal end of the lead via a number of conductors.

In certain applications, the leads are tested for proper positioning and function as part of the implantation process and prior to being connected to the pulse generator, allowing the implanting physician to evaluate pacing and sensing performance prior to concluding that the particular lead position is suitable. During the testing process, for example, a Pacing System Analyzer (PSA) may be connected to the terminal end of the lead to test the connection of the conductor end of the lead to the heart and/or to evaluate the performance of the lead. To facilitate connection of the PSA to the lead, a lead implant tool can be temporarily coupled to the terminal end of the lead, allowing the conductors of the PSA to be connected to the electrical contacts on the terminal end of the lead. In some cases, for example, the implant tool may facilitate the attachment of several alligator clips, plunger clips, or other spring-loaded clips to the electrical contacts on the terminal end of the lead. Examples of lead implant tools for use in connecting the conductors of a PSA to a multi-conductor lead are described in U.S. Patent Publication No. 2005/0177199 to Hansen et al. and U.S. Patent Publication No. 2006/0258193 to Hoecke et al., each of which are incorporated herein by reference in their entirety for all purposes.

More recent trends in lead designs have focused on the development of lead connectors with up to four electrical contacts. The terminal end of such leads are not significantly different in size from previous, IS-1 standard leads, which include only two terminal contacts. Many existing spring-loaded clips used for connecting the PSA to the terminal contacts are often inadequate for use with more modern lead designs, particularly due to the limited spacing between the contacts, and since the space between the contacts is sometimes used as a sealing area to ensure electrical isolation.

SUMMARY

Discussed herein is a lead adapter for testing pacing thresholds across multiple vectors at lead implant, and systems and methods for using the lead adapter for testing pacing thresholds.

In Example 1, an adapter for testing pacing thresholds of an implanted lead with a testing device includes a main body, a connector module, and a switch assembly. The lead includes a plurality of electrodes at a lead distal end electrically coupled to a plurality of connector contacts at a lead proximal end. The adapter main body includes a plurality of adapter contacts configured to electrically couple to the plurality of connector contacts. The connector module includes a first port configured to couple to a first testing device connector and a second port configured to couple to a second testing device connector. A switch assembly includes a plurality of actuatable elements each associated with one of the adapter contacts. The plurality of actuatable elements are each selectably actuatable between a first state that electrically couples the associated adapter contact to the first port, a second state that electrically couples the associated adapter contact to the second port, and a third state that electrically decouples the associated adapter contact from the first and second ports.

In Example 2, the adapter according to Example 1, wherein two or more of the actuatable elements are actuatable to the first state or second state to electrically connect multiple electrodes to the first testing device connector or second testing device connector, respectively, when testing pacing thresholds.

In Example 3, the adapter according to either Example 1 or 2, wherein the first and second testing device connectors comprise conductive clips, and wherein the first and second ports each includes conductive elements configured to interface with the conductive clips.

In Example 4, the adapter according to any of Examples 1-3, wherein the plurality of adapter contacts comprises a plurality of spring contact members.

In Example 5, the adapter according to any of Examples 1-4, wherein the plurality of actuatable elements comprises a plurality of double pole, double throw (DPDT) switches.

In Example 6, the adapter according to any of Examples 1-5, wherein the main body comprises a slot configured to receive a guidewire or stylet.

In Example 7, the adapter according to any of Examples 1-6, wherein the switch assembly further includes an indicator associated with each actuatable element that indicates whether the actuatable element is in the first state, second state, or third state.

In Example 8, a method for using an adapter to test pacing thresholds of an implantable lead with a testing device includes implanting the lead at a location within the body. Each of a plurality of connector contacts at the proximal end of the implanted lead is connected to one of a plurality of adapter contacts on the adapter. A first testing device connector is then coupled to a first port on the adapter and a second testing device connector is coupled to a second port on the adapter. One or more of a plurality of actuatable elements on the adapter are actuated to one of a first state, second state, or third state to select an electrode configuration for pacing threshold testing. The plurality of actuatable elements is each associated with one of the adapter contacts. In the first state each actuatable element electrically couples the associated adapter contact to the first port, in the second state each actuatable element electrically couples the associated adapter contact to the second port, and in the third state each actuatable element electrically decouples the associated adapter contact from the first and second ports.

In Example 9, the method according to Example 8, wherein the actuating step comprises actuating two or more of the actuatable elements to the first state or second state to electrically connect multiple electrodes to the first testing device connector or second testing device connector, respectively, when testing pacing thresholds.

In Example 10, the method according to either Example 8 or 9, wherein the coupling step comprises securing first and second conductive clips to conductive elements on the first and second ports, respectively, that are configured to interface with the conductive clips.

In Example 11, the method according to any of Examples 8-10, wherein the plurality of adapter contacts comprises a plurality of spring contact members.

In Example 12, the method according to any of Examples 8-11, wherein the plurality of actuatable elements comprises a plurality of double pole, double throw (DPDT) switches.

In Example 13, the method according to any of Examples 8-12, wherein the adapter comprises a slot configured to receive a guidewire or stylet during the implanting step.

In Example 14, the method according to any of Examples 8-13, wherein the plurality of actuatable elements each includes an indicator that indicates whether the actuatable element is in the first state, second state, or third state.

In Example 15, an adapter for testing pacing thresholds of an implanted lead with a testing device includes a main body, a connector module, and a switch assembly. The lead includes a plurality of electrodes at a lead distal end electrically coupled to a plurality of connector contacts at a lead proximal end. The adapter main body includes a plurality of adapter contacts configured to electrically couple to the plurality of connector contacts. The connector module includes a plurality of ports each configured to couple to a testing device connector. The switch assembly includes a plurality of switches each associated with one of the adapter contacts. The plurality of switches is each selectably actuatable to electrically connect the associated adapter contact with one of the plurality of ports or to electrically disconnect the associated adapter contact from all ports.

In Example 16, the adapter according to Example 15, wherein two or more of the switches are actuatable to electrically connect multiple electrodes to the same testing device connector when testing pacing thresholds.

In Example 17, the adapter according to either Example 15 or 16, wherein the plurality of testing device connectors each comprises a conductive clip, and wherein each port includes conductive elements configured to interface with the conductive clip.

In Example 18, the adapter according to any of Examples 15-17, wherein the plurality of adapter contacts comprises a plurality of spring contact members.

In Example 19, the adapter according to any of Examples 15-18, wherein the main body comprises a slot configured to receive a guidewire or stylet.

In Example 20, the adapter according to any of Examples 15-19, wherein the switch assembly further includes an indicator associated with each switch that indicates whether the adapter contact is electrically connected to a port and to which port the adapter contact is electrically connected.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
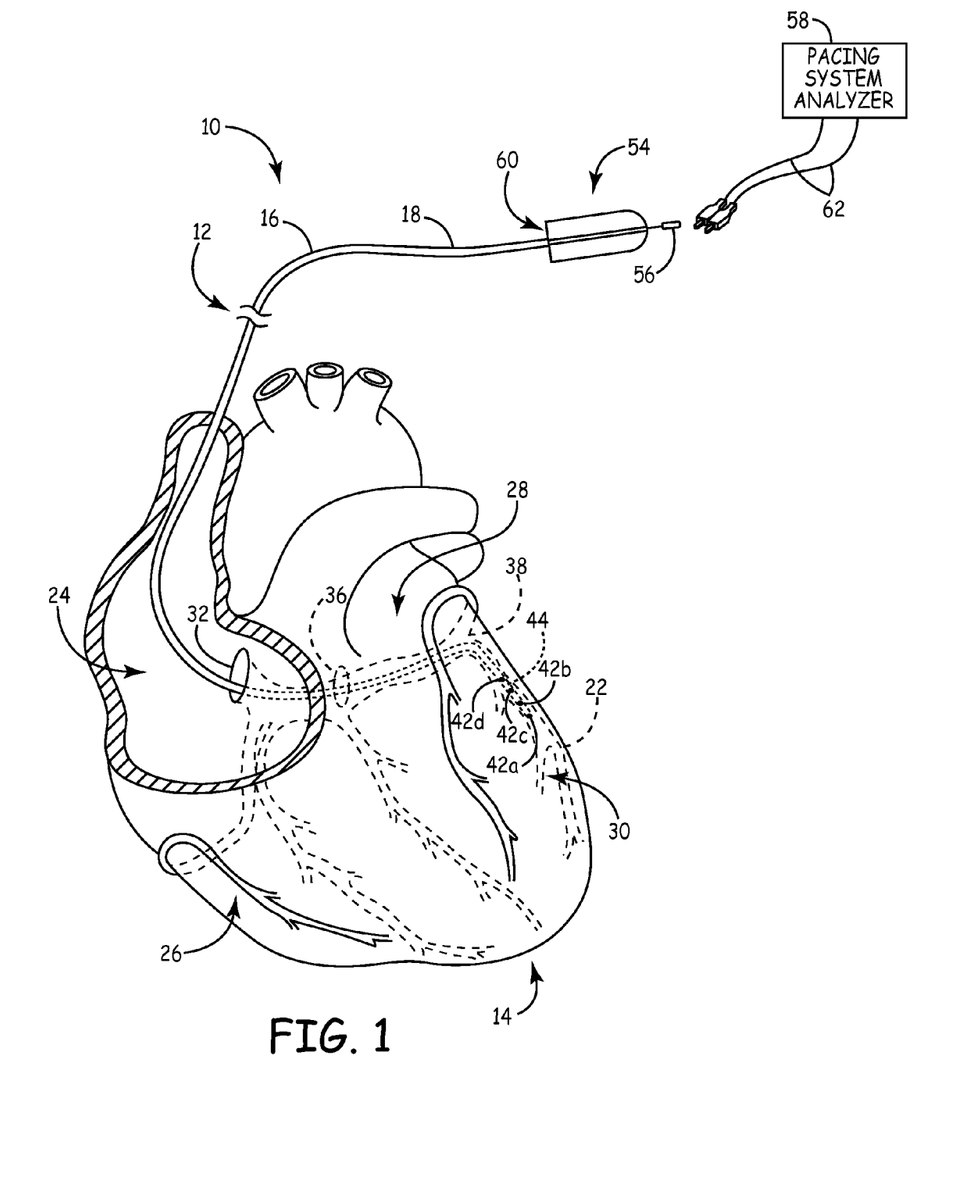
FIG. 1 is a schematic view showing an illustrative system for implanting and testing an implantable lead within the body of a patient.

FIG. 1 is a schematic view showing an illustrative system 10 for implanting and testing an implantable lead 12 within the body of a patient. For purposes of illustration and not limitation, the system 10 is described in conjunction with an implantable lead 12 for use in sensing cardiac electrical activity and/or for providing electrical stimulus therapy to a patient's heart 14. The system 10 can be used in other contexts where implantable leads are employed, and where testing is to be conducted prior to the connection of the lead to another implantable device such as a pulse generator. In certain embodiments, for example, the system 10 can be used to aid in the implantation and testing of an implantable neurostimulation lead prior to its connection to another implantable device such as a pulse generator.

According to various embodiments, the lead 12 includes a lead body 16 extending from a proximal end 18 adapted to be coupled to a pulse generator to a distal end 22. The lead 12 can be implanted in the patient's heart 14, which as shown in FIG. 1, includes a right atrium 24, a right ventricle 26, a left atrium 28, and a left ventricle 30. In the embodiment illustrated in FIG. 1, the distal end 22 of the lead 12 is transvenously guided through the right atrium 24, through the coronary sinus ostium 32, and into a branch of the coronary sinus 36 or great cardiac vein 38. The illustrated position of the lead 12 can be used for sensing or for delivering pacing energy to the left side of heart 14, or to treat arrhythmias or other cardiac disorders requiring therapy delivered to the left side of the heart 14. Additionally, in some embodiments, the lead 12 can be configured to provide treatment in other regions of the heart 14 (e.g., the right atrium 24 or right ventricle 26). The lead 12 can include one or more electrodes 42 for providing electrical therapy to and/or sensing therapy to the patient's heart 14. In certain embodiments, the implantable lead 12 is a quadripolar lead including four electrodes 42a, 42b, 42c, 42d located in a distal region 44 of the lead 12.

Although the illustrative embodiment depicts only a single implantable lead 12 inserted into the patient's heart 14, in other embodiments multiple leads can be utilized so as to electrically stimulate other areas of the heart 14. In some embodiments, for example, the distal section of a second lead (not shown) may be implanted in the right atrium 24 or right ventricle 26 to stimulate the right side of the heart 14. Other types of leads such as epicardial leads may also be utilized in addition to, or in lieu of, the lead 12 depicted in FIG. 1.

In the illustrative embodiment depicted, the system 10 further includes an implant tool 54, a stiffening member such as a stylet or guidewire 56, and a Pacing System Analyzer (PSA) 58 that can be used for implanting and testing the lead 12 within the body. During the course of the procedure, to evaluate the viability of a potential stimulation site, the function and location of the lead 12 can be tested by connecting a proximal, terminal connector 60 located at the proximal end 18 of the lead 12 to several electrical conductors 62 of the PSA 58. This evaluation can be performed after implantation of the lead 12 at the potential stimulation site. Such testing can be performed, for example, to verify that the electrodes 42 are properly positioned on or within the heart 14. The PSA 58 can also be used to perform other functions such as measuring pacing thresholds, lead impedance and r-wave amplitude.

The implant tool 54 can be used with passive fixation leads to enable stylet or guidewire passage and electrical connection while protecting the terminal connector 60. In other embodiments, other fixation mechanisms such as, for example, a fixation helix, can also be deployed via the implant tool 54. The implant tool 54 is configured to permit the implanting physician to easily feed various stylets or guidewires 56 into a pin lumen of the implantable lead 12, to make an electrical connection between the PSA conductors 62 and a terminal pin 64 (FIG. 2) and one or more terminal ring electrodes on the lead 12.

In use, the adapter 54 protects the lead connector throughout the implant procedure from electrical clips or other surgical implements. As such, the adapter 54 is typically removed only after the connection of the device to another implantable device such as a pulse generator is to occur. At that time, the lead adapter 54 is removed from the lead 12, and the lead 12 is then connected to the pulse generator. During normal operation, the lead 12 is configured to convey electrical signals between the pulse generator and the heart 14. For example, in those embodiments where the pulse generator is a pacemaker, the lead 12 can be used to deliver electrical therapeutic stimulus for pacing the heart 14. In some embodiments, the pulse generator includes both pacing and defibrillation capabilities, or is capable of performing biventricular or other multi-site resynchronization therapies such as cardiac resynchronization therapy (CRT). Example leads and lead connectors that can be used in conjunction with the adapter 54 can include, but are not limited to, ICD leads (e.g., including a quadripolar, IS-1/DF-1 or IS-4 type connector), pacing and CRT leads (e.g., including a quadripolar IS-4 connector or IS-1 type connector), and pacing leads with sensing capabilities (e.g., a pressure sensing/pacing lead with a quadripolar type connector). Other types of leads and/or lead connector types can also be used in conjunction with the adapter 54, as desired.

Figure 2:
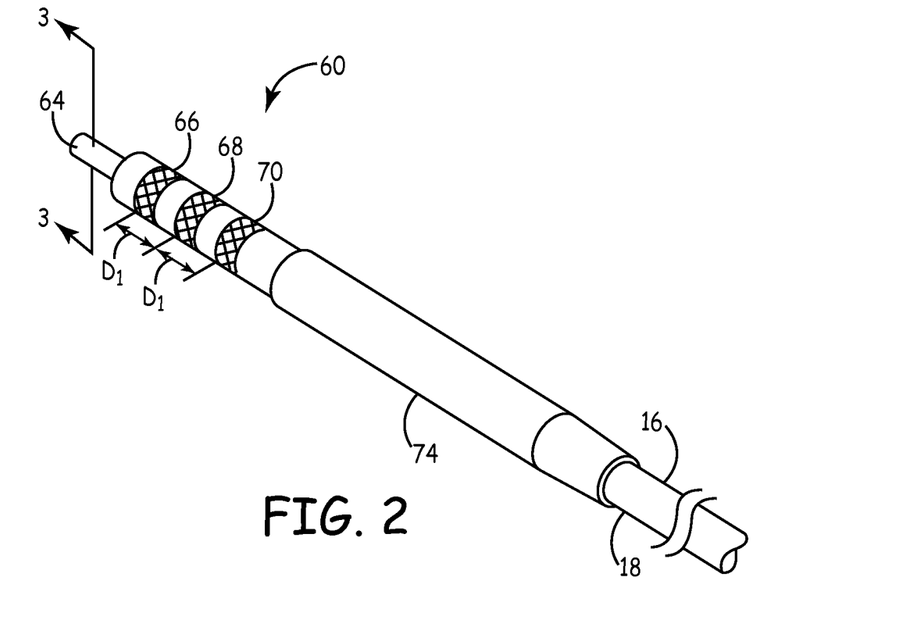
FIG. 2 is a perspective view showing the terminal end of the implantable lead of FIG. 1 in greater detail.

FIG. 2 is a perspective view showing the terminal connector 60 of the implantable lead 12 of FIG. 1 in greater detail. As further shown in FIG. 2, the implantable lead 12 includes a lead terminal pin 64 and a number of terminal rings 66, 68, 70 each spaced axially apart from each other a distance D1 along the length of the lead body 16. In some embodiments, the terminal connector 60 includes an IS-4 type connector. In some embodiments, the terminal pin 64 is coupled to a first, distal most electrode 42a located in the distal region 44 of the lead 12 and serves as the cathode for the implantable lead 12. The first terminal ring 66 may be electrically coupled to a second electrode 42b, which can serve as a cathode or an anode for the implantable lead 12. The second and third terminal ring electrodes 68 and 70 may be electrically coupled, respectively, to third and fourth electrodes 42c and 42d located on a distal region 44 of the implantable lead 12. In some embodiments, the lead body 16 has a circular cross-sectional shape, and includes an enlarged-diameter terminal boot 74 located distally of the terminal rings 66, 68, 70

Various other configurations can also utilize a quadripolar connector such as that shown in FIG. 2. For example, although the implantable lead 12 includes a terminal connector 60 having a terminal pin 64 and three terminal rings 66, 68, 70, in other embodiments the number and configuration of the terminal contacts may vary from that shown. In one embodiment, for example, the implantable lead 12 can comprise a bi-polar pacing lead including a terminal connector having a single terminal pin and ring electrode. In another example, a shocking coil in the right ventricle 26 can serve the dual purpose of a rate/sense anode as well as a shocking coil for defibrillation. In this configuration, which is typical for an integrated bipolar lead, ring 66 and ring 68 can be connected together. Additionally, in some ICD leads that include a shocking coil in only the right ventricle 26, the terminal ring 70 may not be connected to a conductor. In a further example, the implantable lead 12 can comprise an atrial synchronous, ventricular pacing (VDD) or single pass lead having two right ventricle (RV) electrodes and two right atrium (RA) electrodes. Other lead configurations are also possible.

Figure 3:
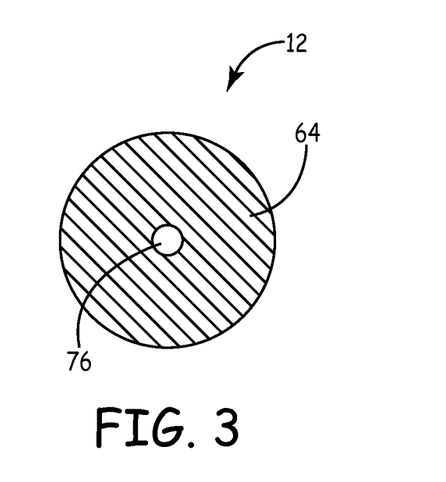
FIG. 3 is a transverse cross-sectional view showing the implantable lead across line 3-3 in FIG. 2.

FIG. 3 is a transverse cross-sectional view showing the implantable lead 12 across line 3-3 in FIG. 2. In certain embodiments, the terminal pin 64 includes a pin lumen 76 sized and shaped to allow various stylets or guidewires (e.g., stylet 56) to be inserted through the implantable lead 12 during the implantation procedure.

Figure 4A:
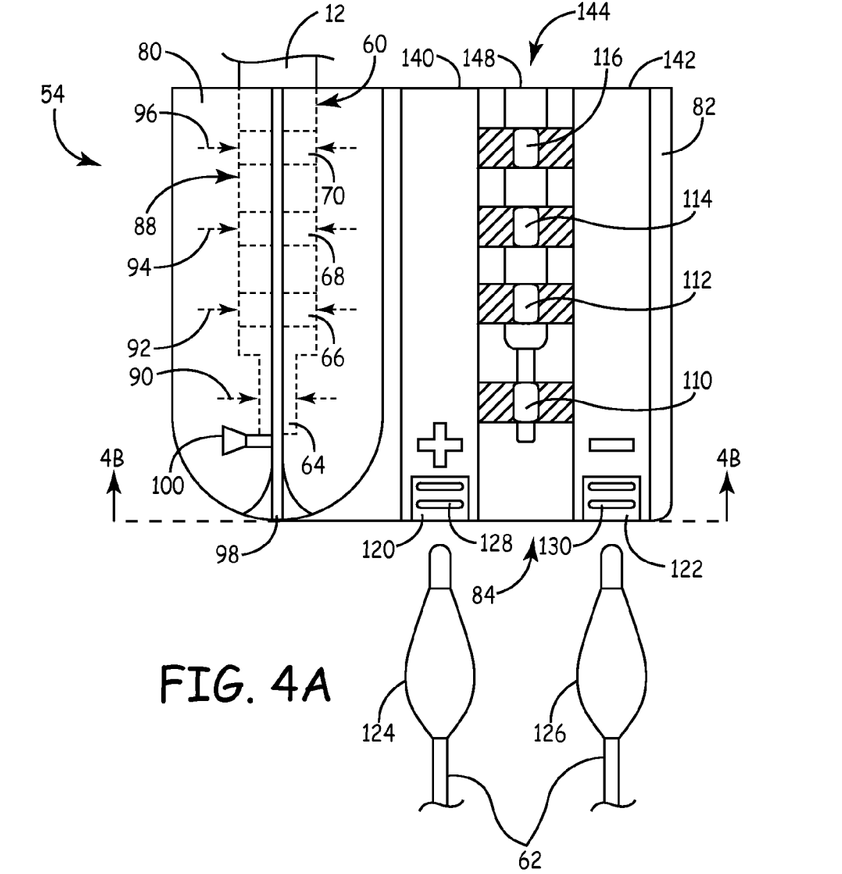
FIG. 4A is a side view showing a lead adapter for testing pacing thresholds at implant in accordance with an illustrative embodiment.
Figure 4B:
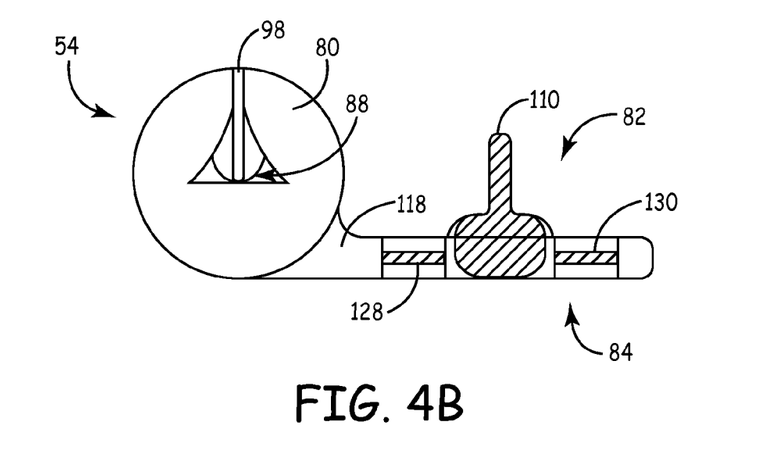
FIG. 4B is an end view of the lead adapter shown in FIG. 4A.

FIG. 4A is a side view and FIG. 4B is an end view (from line 4B-4B in FIG. 4A) of an embodiment of the adapter 54 for testing pacing thresholds after implanting the lead 12. The adapter 54 includes a main housing 80, a switch assembly 82, and a connector module 84. In some embodiments, the main housing 80, switch assembly 82, and connector module 84 are comprised of sterilizable materials.

The main housing 80 includes a cylindrical or rounded body, a lumen 88 configured to receive the terminal connector 60 of the lead 12, a plurality of adapter contacts 90, 92, 94, and 96 in the lumen 88, and a slot 98 configured to receive the stylet or guidewire 56 (FIG. 1). The slot 98 allows adapter 54 to be coupled to the terminal connector 60 while the stylet or guidewire 56 is inserted into the pin lumen 76 during implantation of the lead 12. That is, the stylet or guidewire 56 may be slid through the slot 98 when the adapter 54 is being coupled to the terminal connector 60.

The adapter contacts 90, 92, 94, and 96 are arranged in the lumen 88 such that, when the terminal connector 60 is inserted into the lumen 88, the adapter contacts 90, 92, 94, 96 electrically couple with the lead terminal pin 64 and terminal rings 66, 68, 70, respectively. In some embodiments, the adapter contacts 90, 92, 94, 96 are spring contacts. For example, the spring contacts may be similar to those described in U.S. application Ser. No. 13/267,572, filed Oct. 6, 2011, entitled "Multi-Function Lead Implant Tool," which is herein incorporated by reference in its entirety. While four adapter contacts 90, 92, 94, 96 are shown, the adapter 54 may alternatively include more or fewer adapter contacts to accommodate lead terminal ends with different numbers of lead contacts.

The main housing 80 may further include an indicator 100 that indicates when the terminal connector 60 is fully inserted into the lumen 88 of the adapter 54, and thus electrically connected to the adapter contacts 90, 92, 94, 96. In some embodiments, the indicator 100 is an opening or window in the main housing 80 that allows the clinician to see the terminal connector 60 when the lead 12 is fully inserted into the adapter 54. In some embodiments, the indicator 100 is a light emitting diode, or a mechanism that changes color when the terminal connector 60 is fully inserted into the adapter 54.

The switch assembly 82 extends from the main housing 80 and includes a plurality of actuatable elements 110, 112, 114, 116. The number of actuatable elements 110, 112, 114, 116 are electrically coupled to the adapter contacts 90, 92, 94, 96, respectively, through a coupling interface 118 that extends between the main housing 80 and switch assembly 82. In the illustrated embodiment, the actuatable elements 110, 112, 114, 116 are switches actuatable between a plurality of positions corresponding to different coupling states. In some embodiments, the switches are double pole, double throw (DPDT) switches. A schematic illustrating the connectivity between the adapter contacts 90, 92, 94, 96 and the actuatable elements 110, 112, 114, 116 is described herein with respect to FIG. 5. The actuatable elements 90, 92, 94, and 96 may alternatively include other electrical coupling elements, such as dials, sliders, buttons, and the like. While four actuatable elements 110, 112, 114, 116 are shown, the switch assembly 82 may alternatively include more or fewer actuatable elements electrically coupled to a corresponding number of adapter contacts. In addition, while the switch assembly 82 is shown extending from the main housing 80, the switch assembly 82 may alternatively be integrated into the main housing 80.

The connector module 84 includes ports 120 and 122, which are configured to electrically couple with connectors 124, 126 associated with the electrical conductors 62 of the PSA 58 (FIG. 1). In the illustrated embodiment, the connectors 124, 126 are conductive clips (e.g., alligator clips), and the ports 120, 122 include conductive elements 128, 130, respectively, to which the conductive clips attach. The conductive elements 128, 130 may be conductive bars or plates to which the conductive clips couple, for example. Other types of electrical interfaces between the connectors 124, 126 and ports 120, 122 are also contemplated.

The ports 120, 122 are each electrically coupled to a node of each of the actuatable elements 110, 112, 114, 116. That is, the conductive element 128 of the port 120 is electrically connected to one node of the actuatable elements 110, 112, 114, 116, and the conductive element 130 of the port 122 is electrically connected to another node of the actuatable elements 110, 112, 114, 116. In this configuration, the actuatable elements 110, 112, 114, 116 are each actuatable to a first state, in which the associated adapter contact 90, 92, 94, 96 is electrically connected to the port 120, and a second state, in which the associated adapter contact 90, 92, 94, 96 is electrically connected to the port 122. In the first state, the actuatable element may be connected such that the port 120 is the anode and port 122 is the cathode, while in the second state, the actuatable element may be connected such that the port 122 is the anode and port 120 is the cathode. In some embodiments, the actuatable elements 110, 112, 114, 116 are further each actuatable to a third state, in which the associated adapter contact 90, 92, 94, 96 is electrically disconnected from either port 120 or 122.

While the connector module 84 includes two ports 120, 122 in the illustrated embodiment, the connector module 84 may alternatively include additional ports to accommodate additional connections to the PSA 58. In these embodiments, the actuatable elements 110, 112, 114, 116 may include additional actuation states to allow for connection to the additional ports.

The adapter 54 may include various features to enhance the usability of the adapter 54. In some embodiments, portions 140, 142 of the switch assembly 82 adjacent the actuatable elements 110, 112, 114, 116 and extending from the ports 120, 122, respectively, is color coded. The color coding may correspond to the color of the connectors 124, 126 from the PSA 58 to assure the connectors 124, 126 are connected to the appropriate ports 120, 122. In one exemplary implementation, portion 140 and the connector 124 is red and the portion 142 and the connector 126 is black. The portions 140, 142 may further include a text or graphic labels. In the illustrated embodiment, the portion 140 includes a label "+" and the portion 142 includes a label "−", but other text labels are also possible (e.g., anode, cathode).

In addition, the region 144 on the switch assembly 82 between the portions 140, 142, which houses the actuatable elements 110, 112, 114, 116, may include a graphical representation 148 of the terminal connector 60. The locations of the actuatable elements 110, 112, 114, 116 on the graphical representation 148 may correspond to the locations of the contacts 64, 66, 68, 70 on the terminal connector 60 of the lead 12. The actuatable elements 110, 112, 114, 116 may each include associated indicators to indicate whether each actuatable element 110, 112, 114, 116 is connected to the port 120, connected to the port 122, or disconnected from both ports 120, 122. For example, actuating the actuatable elements 110, 112, 114, 116 may expose a colored portion of the actuatable element 110, 112, 114, 116 that corresponds to the color of the portions 140, 142. As another example, each actuatable element 110, 112, 114, 116 may have one more lights (e.g., light emitting diodes) that indicate the state of the associated actuatable element 110, 112, 114, 116.

Furthermore, the actuating elements 110, 112, 114, 116 may be configured to assist the clinician in identifying each actuating element 110, 112, 114, 116 without looking at the adapter 54. For example, one or more of the actuating elements 110, 112, 114, 116 may be sized differently, may include a different texture, and/or be spaced differently from the adjacent actuating elements 110, 112, 114, 116.

Figure 5:
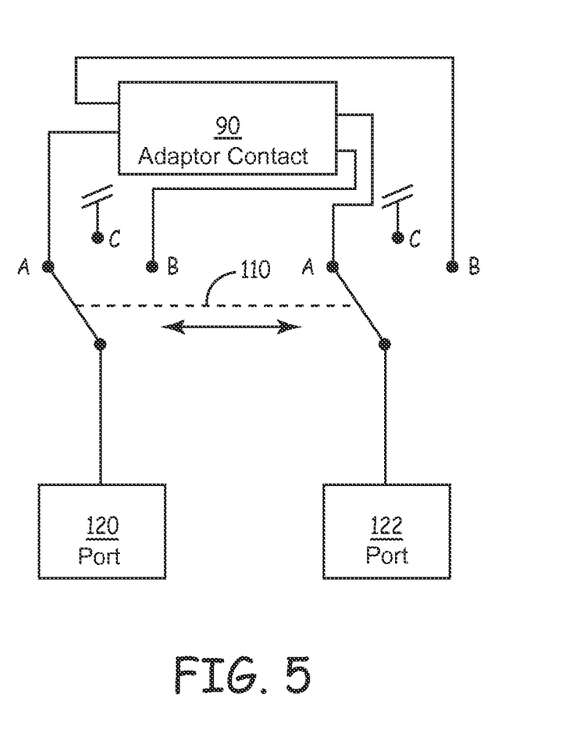
FIG. 5 is a schematic of a circuit including a spring contact couplable to contacts on the proximal end of an implantable lead and connected to a double pole, double throw (DPDT) switch.

FIG. 5 is a schematic of circuit including the adapter contact 90 electrically coupled to an actuatable element 110 that is switchable between port 120, port 122, and electrically disconnected from ports 120 and 122. In the illustrated embodiments, the actuatable element 110 is a DPDT switch. The connectivity between adapter contacts 92, 94, 96, actuatable elements 112, 114, 116, respectively, and ports 120, 122 may be similarly illustrated. In the first state, the DPDT switch 110 connects the ports 120, 122 to nodes A of the adapter contact 90. In the second state, the DPDT switch 110 connects the ports 120, 122 to nodes B of the adapter contact 90. In the third state, the DPDT switch 110 is connected to node C, which is electrically disconnected from the ports 120 and 122.

Referring back to FIGS. 4A and 4B, in use, the lead 12 is implanted at a location within the body, and the adapter 54 is connected to the terminal connector 60 as described above. The connectors 124, 126 of the PSA 58 are then coupled to the conductive elements 128, 130, respectively, to electrically connect the ports 120, 122 to the PSA 58. The actuatable elements 110, 112, 114, 116 are then selectably actuated to electrically connect one or more of the adapter contacts 90, 92, 94, 96 to each of the ports 120, 122. This selects the cathode and anode electrode(s) at the distal end of the lead 12 for determining pacing thresholds by delivering signals to the anode/cathode electrodes and taking electrical readings across the anode/cathode electrodes. The actuatable elements 110, 112, 114, 116 can be actuated to test multiple pacing vectors by varying the electrodes that are set as the anode and cathode.

It may be desirable to use one or more electrodes on a second lead located in a different portion of the heart 14 as the anode or cathode during pacing threshold testing. In this case, the appropriate connector 124 or 126 is coupled to the contact on the second lead's terminal end that corresponds to selected one or more electrodes on the second lead. Alternatively, the adapter 54 may be configured to couple with two or more leads and may include additional or other types of actuatable elements to allow for connection of each of the electrodes on each of the leads to ports 120, 122.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. An adapter for testing pacing thresholds of an implanted lead with a testing device, the testing device having a first testing device connector and a second testing device connector, the lead including a plurality of electrodes at a lead distal end electrically coupled to a plurality of connector contacts at a lead proximal end, the adapter comprising:
   a main body including a plurality of adapter contacts, the plurality of adapter contacts configured to electrically couple to the plurality of connector contacts;
   a connector module including a first port configured to couple to the first testing device connector of the testing device and a second port configured to couple to the second testing device connector of the testing device; and
   a switch assembly including a plurality of actuatable elements each associated with one of the adapter contacts, the plurality of actuatable elements each selectably actuatable between three different actuation positions respectively corresponding to a first state, a second state, and a third state, the first state electrically coupling the associated adapter contact to the first port, the second state electrically coupling the associated adapter contact to the second port, and the third state electrically decoupling the associated adapter contact from the first and second ports.

2. The adapter of claim 1, wherein two or more of the actuatable elements are actuatable to the first state or second state to electrically connect multiple electrodes to the first testing device connector or second testing device connector, respectively, when testing pacing thresholds.

3. The adapter of claim 1, wherein the first and second testing device connectors comprise conductive clips, and wherein the first and second ports each includes conductive elements configured to interface with the conductive clips.

4. The adapter of claim 1, wherein the plurality of adapter contacts comprises a plurality of spring contact members.

5. The adapter of claim 1, wherein the plurality of actuatable elements comprises a plurality of double pole, double throw (DPDT) switches.

6. The adapter of claim 1, wherein the main body comprises a slot configured to receive a guidewire or stylet.

7. The adapter of claim 1, wherein the switch assembly further includes an indicator associated with each actuatable element that indicates whether the actuatable element is in the first state, second state, or third state.

8. A method for using an adapter to test pacing thresholds of an implantable lead with a testing device, the testing device having a first testing device connector and a second testing device connector, the implantable lead including a plurality of electrodes at a lead distal end electrically coupled to a plurality of connector contacts at a lead proximal end, the method comprising:
   implanting the lead at a location within the body;
   coupling each of the plurality of connector contacts to one of a plurality of adapter contacts on the adapter;
   coupling the first testing device connector to a first port on the adapter and the second testing device connector to a second port on the adapter; and
   actuating one or more of a plurality of actuatable elements on the adapter between three different actuation positions respectively corresponding to a first state, a second state, and a third state to select an electrode configuration for pacing threshold testing, the plurality of actuatable elements each associated with one of the adapter contacts, wherein in the first state each actuatable element electrically couples the associated adapter contact to the first port, in the second state each actuatable element electrically couples the associated adapter contact to the second port, and in the third state each actuatable element electrically decouples the associated adapter contact from the first and second ports.

9. The method of claim 8, wherein the actuating step comprises actuating two or more of the actuatable elements to the first state or second state to electrically connect multiple electrodes to the first testing device connector or second testing device connector, respectively, when testing pacing thresholds.

10. The method of claim 8, wherein the coupling step comprises securing first and second conductive clips to conductive elements on the first and second ports, respectively, that are configured to interface with the conductive clips.

11. The method of claim 8, wherein the plurality of adapter contacts comprises a plurality of spring contact members.

12. The method of claim 8, wherein the plurality of actuatable elements comprises a plurality of double pole, double throw (DPDT) switches.

13. The method of claim 8, wherein the adapter comprises a slot configured to receive a guidewire or stylet during the implanting step.

14. The method of claim 8, wherein the plurality of actuatable elements each includes an indicator that indicates whether the actuatable element is in the first state, second state, or third state.

15. An adapter for testing pacing thresholds of an implanted lead with a testing device, the lead including a plurality of electrodes at a lead distal end electrically coupled to a plurality of connector contacts at a lead proximal end, the adapter comprising:
   a main body including a plurality of adapter contacts, the plurality of adapter contacts configured to electrically couple to the plurality of connector contacts;

a connector module including a plurality of ports each configured to couple to a testing device connector; and a switch assembly including a plurality of switches each associated with one of the adapter contacts, the plurality of switches each selectably actuatable between three different actuation positions to electrically connect the associated adapter contact with one of the plurality of ports or to electrically disconnect the associated adapter contact from all ports.

16. The adapter of claim 15, wherein two or more of the switches are actuatable to electrically connect multiple electrodes to the same testing device connector when testing pacing thresholds.

17. The adapter of claim 15, wherein the plurality of testing device connectors each comprises a conductive clip, and wherein each port includes conductive elements configured to interface with the conductive clip.

18. The adapter of claim 15, wherein the plurality of adapter contacts comprises a plurality of spring contact members.

19. The adapter of claim 15, wherein the main body comprises a slot configured to receive a guidewire or stylet.

20. The adapter of claim 15, wherein the switch assembly further includes an indicator associated with each switch that indicates whether the adapter contact is electrically connected to a port and to which port the adapter contact is electrically connected.

* * * * *